US008282965B2

(12) United States Patent
de Kort et al.

(10) Patent No.: US 8,282,965 B2
(45) Date of Patent: Oct. 9, 2012

(54) LIQUID NUCLEOTIDES/NUCLEOSIDES-CONTAINING PRODUCT

(75) Inventors: Esther Jacqueline de Kort, Wageningen (NL); Robert Johan Joseph Hageman, Wageningen (NL); Martine Groenendijk, Barendrecht (NL); Patrick Joseph Gerardus Hendrikus Kamphuis, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 206 days.

(21) Appl. No.: 12/809,418

(22) PCT Filed: Mar. 4, 2008

(86) PCT No.: PCT/NL2008/050124
§ 371 (c)(1),
(2), (4) Date: Sep. 15, 2010

(87) PCT Pub. No.: WO2009/082203
PCT Pub. Date: Jul. 2, 2009

(65) Prior Publication Data
US 2011/0027391 A1 Feb. 3, 2011

(30) Foreign Application Priority Data
Dec. 20, 2007 (EP) .................................... 07123811

(51) Int. Cl.
*A01N 59/06* (2006.01)
*A61K 33/06* (2006.01)

(52) U.S. Cl. ....... 424/682; 514/17.8; 514/17.7; 514/1.1; 514/44 R

(58) Field of Classification Search .................. None
See application file for complete search history.

(56) References Cited

U.S. PATENT DOCUMENTS

| 3,600,197 | A | 8/1971 | Spangler et al. |
| 5,886,037 | A | 3/1999 | Klor et al. |
| 6,689,467 | B1 | 2/2004 | Joubert et al. |
| 6,835,750 | B1 | 12/2004 | Henderson |
| 7,090,879 | B2 | 8/2006 | Albrecht et al. |
| 2004/0001817 | A1 | 1/2004 | Giampapa |
| 2006/0025376 | A1* | 2/2006 | Wurtman ..................... 514/51 |
| 2007/0004670 | A1 | 1/2007 | Wurtman et al. |
| 2007/0140992 | A1 | 6/2007 | Schick et al. |
| 2010/0323982 | A1 | 12/2010 | Hageman et al. |
| 2010/0331258 | A1 | 12/2010 | Kamphuis et al. |
| 2010/0331275 | A1 | 12/2010 | Groenendijk et al. |
| 2011/0006917 | A1 | 1/2011 | Taniguchi et al. |
| 2011/0009357 | A1 | 1/2011 | Hageman et al. |
| 2011/0105594 | A1 | 5/2011 | De Kort et al. |

FOREIGN PATENT DOCUMENTS

| EP | 0 175 468 | A2 | 3/1986 |
| EP | 1 216 041 | B1 | 6/2002 |
| EP | 1 282 365 | B1 | 2/2003 |
| EP | 1 656 839 | A1 | 5/2006 |
| EP | 1 666 092 | A2 | 6/2006 |
| EP | 1 800 675 | A1 | 6/2007 |
| JP | 64-080250 | A | 3/1989 |
| JP | 06-237734 | A | 8/1994 |
| JP | 10-004918 | A | 1/1998 |
| JP | 10-136937 | A | 5/1998 |
| JP | 11-071274 | A | 3/1999 |
| WO | WO-00/38829 | A1 | 7/2000 |
| WO | WO-01/32034 | A1 | 5/2001 |
| WO | WO-02/088159 | A1 | 11/2002 |
| WO | WO-02/096464 | A1 | 12/2002 |
| WO | WO-03/013276 | A1 | 2/2003 |
| WO | WO-03/041701 | A2 | 5/2003 |
| WO | WO-2005/039597 | A2 | 5/2005 |
| WO | WO-2006/031683 | A2 | 3/2006 |
| WO | WO-2006/118665 | A2 | 11/2006 |
| WO | WO-2006/127620 | A2 | 11/2006 |
| WO | WO-2007/001883 | A2 | 1/2007 |
| WO | WO-2007/004685 | A2 | 1/2007 |
| WO | WO-2007/004689 | A1 | 1/2007 |
| WO | WO-2007/008586 | A2 | 1/2007 |
| WO | WO-2007/058538 | A2 | 5/2007 |
| WO | WO-2007/073178 | A2 | 6/2007 |
| WO | WO-2009/002145 | A1 | 12/2008 |
| WO | WO-2009/002146 | A1 | 12/2008 |
| WO | WO-2009/002148 | A1 | 12/2008 |

(Continued)

OTHER PUBLICATIONS

Database WPI Week 198918, Derwent Publications Ltd., London, GB, AN 1989-134762, JP 01 080250, Mar. 27, 1989 [XP002449815].
Database WPI Week 199439, Thomson Scientific, London, GB, AN 1994-312783, JP 06 237734, Aug. 30, 1994 [XP002494932], 2 pages.
Database WPI Week 199182, Derwent Publications Ltd., London, GB, AN 1998-123754, JP 10 004918, Jan. 13, 1998 [XP002470089], 1 page.
Database WPI Week 199831, Derwent Publications Ltd., London, GB, AN 1998-355002, JP 10 136937, May 26, 1998 [XP002449814].
Database WPI Week 199921, Thomson Scientific, London, GB, AN 1999-248435, JP 11 071274, Mar. 16, 1999 [XP002495741].

(Continued)

*Primary Examiner* — Johann Richter
*Assistant Examiner* — Daniel L Branson
(74) *Attorney, Agent, or Firm* — Giberto M. Villacorta; Sunit Talapatra; Foley & Lardner LLP

(57) ABSTRACT

The invention pertains to a liquid composition for preventing and/or treating memory decline and/or cognitive dysfunction, Alzheimer's, Parkinson's and/or dementia, said composition comprising: (i) at least 50 mg nucleoside and/or nucleotide per 100 ml; (ii) between 0.2 and 10 grams protein per 100 ml; (iii) between 0.05 and 3 wt. % of 5 thickener, based on total weight of the composition. The thickener is preferably selected from the group consisting of cellulose, xanthan gum, gellan gum, alginate, guar gum, locust bean gum, gum karaya, gum tragacanth, carrageenan, and mixtures thereof. The composition preferably has a loss factor tan δ between 0.1 and 100, as measured at any strain in the range of 1 100% at 0.1 Hz and 20° C. It is particularly found that a thickener selected from the group consisting of gellan gum, xanthan gum and cellulose greatly reduces sedimentation.

33 Claims, No Drawings

FOREIGN PATENT DOCUMENTS

| | | | |
|---|---|---|---|
| WO | WO-2009/002163 | A1 | 12/2008 |
| WO | WO-2009/002164 | A1 | 12/2008 |
| WO | WO-2009/002165 | A1 | 12/2008 |
| WO | WO-2009/002166 | A1 | 12/2008 |
| WO | WO-2009/082227 | A1 | 7/2009 |

OTHER PUBLICATIONS

Folstein et al., "'Mini-Mental State' A Practical Method for Grading the Cognitive State of Patients for the Clinician," J Psychiat Res, 1975, 12(3), pp. 189-198.

Galasko et al., "An Inventory to Assess Activities of Daily Living for Clinical Trials in Alzheimer's Disease," Alz Dis Assoc Dis, 1997, 11(Sup 2), pp. 33-39.

Hansson et al., "Association Between CSF Biomarkers and Incipient Alzheimer's Disease in Patients with Mild Congnitive Impairment: A Follow-up Study," Lancet Neurol, vol. 5, No. 3, 2006, pp. 228-234.

International Search Report for PCT/NL2008/050124, mailed Dec. 29, 2008.

McKahnn et al., "Clinical diagnosis of Alzheimer's disease: Report-of the NINCDS-ADRDA Work Group," Neurology, 1984, 34, pp. 939-944.

Pratico et al., "Increase of Brain Oxidative Stress in Mild Cognitive Impairment," Arch Neurol, Vo. 59, 2002, pp. 972-976.

Wurtman et al., "Synaptic Proteins and Phospholipids are Increased in Gerbil Brain by Administering Uridine Plus Docosahexaenoic Acid Orally," Brain Research, 2006, 1088(1), pp. 83-92.

* cited by examiner

LIQUID NUCLEOTIDES/NUCLEOSIDES-CONTAINING PRODUCT

FIELD OF THE INVENTION

The invention pertains to a liquid nucleotides/nucleosides-containing nutritional product, preferably a product containing uridine-containing nucleotides/nucleosides, and its preparation, and to its use in improving neurodegenerative disorders, preferably for combating memory decline and/or cognitive dysfunction, Alzheimer's, Parkinson's and/or dementia, and for promoting or supporting healthy brain function.

BACKGROUND OF THE INVENTION

Memory loss, dementia and reduced brain function are major problems, particularly in elderly. Significant effort is put in the treatment and/or prevention of these disorders related with impaired nerve functioning. Persons older than 50 years of age are particularly prone to developing such disorders.

WO-A-2006/031683 teaches to administer a composition comprising a uridine in order to improve cognitive and neurological functions in a subject. Uridine, in particular in the form of uridine monophosphate (UMP), is a nutrient that increases synthesis and release of neurotransmitters and membrane synthesis by neural cells and brain cells. Nutritional products containing uridine and high concentrations of macro- and micronutrients are administered to elderly patients, with the aim to prevent memory decline.

However, when targeting this group of patients often troubled by reduced appetite or disturbed eating behavior, such a nutritional product needs to satisfy a number of requirements. It should be readily consumable, thus avoiding an insufficient intake of the active ingredients. For that purpose, it is strived for a product that is desirably liquid with a sufficiently low viscosity so it can be easily swallowed.

SUMMARY OF THE INVENTION

It is desirable to administer active ingredients to elderly and Alzheimer patients in liquid form. Furthermore, it is highly desirable to administer the active ingredients in a relatively small dosage form such that the administration does not interfere with normal nutritional intake. Additionally palatability is of utmost importance to ensure compliance products need to be consumed for many day, weeks, months or years.

Hence, based on the knowledge that nucleosides/nucleotides, particularly uridine- and/or cytidine-containing nucleotides, are advantageously used by patients suffering from memory impairment, the present inventors designed a liquid composition containing uridine monophosphate suitable for administration to elderly and Alzheimer patients, i.e. a liquid composition prepared by admixing different ingredients including a large amount of uridine monophosphate, proteins and preferably also minerals.

However, unexpectedly sediment was formed in the liquid product after several weeks. Sediment is highly undesirable as it reduces shelf life and palatability of the product, and may result in intake of active ingredients at different concentrations. It is the first time that this problem is recognized in the art for this type of product, high in nucleotides and/or nucleosides.

The sediment was most probably caused by a combination of the high concentrations of uridine phosphates and minerals in the composition. Analyses for the sediment revealed that the sediment contains high quantities of calcium, presumably in the form of an insoluble organic salt, e.g. calcium citrate. Calcium citrate is typically added to the composition to include advantageous amounts calcium in the composition. Hence, it would be one solution to reduce the calcium citrate addition or replace the calcium citrate for a different calcium salt. However, this did not appear an option. Addition of other calcium salts resulted in different problems, e.g. addition of a soluble calcium salt resulted in aggregation of proteins which is highly undesirable. Addition of the (insoluble) calcium phosphate also was not an option as it would result in an undesirable intake of phosphorus (i.e. the nucleotides and often proteins already provide high amounts of phosphorus). Reduction of calcium addition would result in an unacceptable lack of calcium in the product. Hence, a particular problem to be solved now was to prevent sediment formation while maintaining palatability and liquidity of the product. Additionally, the product showed a good homogeneity.

Surprisingly it was found that inclusion of a thickener, preferably a thickener selected from the group consisting of cellulose, xanthan gum, gellan gum, alginate, guar gum, locust bean gum, gum karaya, gum tragacanth, carrageenan, and mixtures thereof, especially cellulose, gellan gum and/or xanthan gum, provided an advantageous solution to the problem. It was found that particle formation and subsequent sedimentation was prevented if these thickeners were added to the product. The inventors hypothesize that due to the high viscosity at low shear rate the interactions between minerals, and hence the ability to form sediment particles is limited. Furthermore, the present stabilizer provides a low viscosity when ingested, resulting in a good palatability and easy ingestion for the elderly or Alzheimer or Parkinson patient. This is due to the shear-thinning and/or thixotropic properties of the product with these thickeners.

Hence the present inventors found that a liquid nucleotide-containing nutritional product, in particular a product which comprises a component which comprises a uridine nucleotide, may be provided which is readily consumable and wherein settlement of solids is reduced or even avoided by making use of thickeners, preferably thickeners which demonstrate thixotropic or shear-thinning behavior when added to a liquid. The nutritional formula is pourable, yet is able to hold the nucleotides and further components, among which choline salts, in suspension without the formation of a sediment that is not readily redispersible.

The present solution also works for liquid compositions that contain nucleosides and/or nucleotides other than uridine phosphates, particularly other nucleotides, e.g. cytidine phosphates.

In a further aspect the present inventors found that in a protein-containing composition the aforementioned nucleosides and/or nucleotides, particularly nucleotides, can be suitably used to reduce protein aggregation. Hence, the present invention also provides a thixotropic and/or shear-thinning liquid comprising nucleoside and/or nucleotide and protein, wherein the nucleoside and/or nucleotide provides at least 25 wt. % of the total phosphorus in the composition, preferably at least 30 wt. %.

In yet another aspect the invention pertains to a nutritional composition comprising a nucleotide and a thickener characterized in that the nucleotide provides more than 30 wt. % of the amount of phosphorous that is present in the total composition, and the composition comprises 30 to 80 mg phosphorus per 100 kcal. The composition preferably comprises protein, preferably intact protein, and/or one or more minerals.

DETAILED DESCRIPTION OF THE INVENTION

In one aspect the present invention provides a liquid composition for preventing and/or treating neurodegenerative disorders, preferably selected from the group consisting of memory decline, cognitive dysfunction, Alzheimer's, Parkinson's and/or dementia, said composition comprising: at least 50 mg nucleoside and/or nucleotide per 100 ml; and between 0.2 and 10 grams protein per 100 ml.

In a further aspect the present method provides a method for the treatment and/or prevention of memory decline and/or cognitive dysfunction, Alzheimer's, Parkinson's and/or dementia, said method comprising the administration of a composition comprising: at least 50 mg nucleoside and/or nucleotide per 100 ml; and between 0.2 and 10 grams protein per 100 ml.

In yet a further aspect the present invention provides a liquid comprising at least 50 mg nucleoside and/or nucleotide per 100 ml; and between 0.2 and 10 grams protein per 100 ml.

In still a further aspect, the present invention provides at least 50 mg nucleoside and/or nucleotide per 100 ml, and between 0.2 and 10 grams protein per 100 ml.

The aforementioned liquid compositions are preferably characterized by having a loss factor tan $\delta$ between 0.1 and 100, as measured at any strain in the range of 1-100% at 0.1 Hz and 20° C.

The liquid composition is preferably characterized by having (a) a nucleotide content providing at least 25 wt. % of the total phosphorus in the composition, preferably at least 30 wt. % or (b) a weight ratio of protein to calcium of at least 5, preferably at least 10, more preferably at least 25.

In one aspect, the nucleotide present in the liquid composition provides at least 25 wt. % of the total phosphorus in the composition, preferably at least 30 wt %, more preferably at least 35 wt. %, more preferably 40 to 90 wt. %, most preferably 50 to 85 wt. %.

The use of the present compositions in a method for preventing and/or treating neurodegenerative disorders, preferably selected from the group consisting of memory decline and/or cognitive dysfunction, Alzheimer's, Parkinson's and/or dementia is also provided.

In a further aspect the present invention provides a nutritional composition comprising a nucleotide and a thickener characterized in that the nucleotide provides more than 30 wt. %, preferably 40-90, more preferably 50-85 wt. %, of the amount of phosphorous that is present in the total composition, and the composition comprises 30 to 80 mg phosphorus per 100 kcal.

Thickener

The present composition contains a thickener. Preferably the present composition contains a thickener selected from the group consisting of xanthan gum, gellan gum, cellulose, alginate, guar gum, locust bean gum, gum karaya, gum tragacanth, carrageenan, and mixtures thereof.

More preferably the present composition comprises a thickener selected from the group consisting of xanthan gum, gellan gum and cellulose. These thickeners preferably have shear-thinning and/or thixotropic properties which are considered beneficial to the product. It is even more preferred that the thickener is selected from the group consisting of xanthan gum and cellulose. Most preferably the present composition comprises cellulose. According to a preferred embodiment, the present composition contains at least 70 wt. % cellulose based on total weight of thickener.

Preferably the present composition contains between 0.05 and 3 wt. % of one or more of the aforementioned thickeners, based on total weight of the composition, preferably 0.1-2 wt. %, more preferably 0.3-1 wt. %.

One of the preferred thickeners is the polysaccharide xanthan gum. Its backbone consists of two $\beta$-D-glucose units linked through the 1 and 4 positions. The side chain consists of two mannose and one glucuronic acid, so the chain consists of repeating modules of five sugar units. The side chain is linked to every other glucose of the backbone at the 3 position. About half of the terminal mannose units have a pyruvic acid group linked as a ketal to its 4 and 6 positions. The other mannose unit has an acetyl group at the 6 positions. It is preferred to use xanthan gum having pseudoplastic behaviour, and which is stable over a wide range of temperatures and pH.

Gellan gum is a linear tetrasaccharide 4)-L-rhamnopyranosyl-($\alpha$-1$\rightarrow$3)-D-glucopyranosyl-($\beta$-1$\rightarrow$4)-D-glucuronopyranosyl-($\beta$-1$\rightarrow$4)-D-glucopyranosyl-($\beta$-1$\rightarrow$ with O(2) L-glyceryl and O(6) acetyl substituents on the 3-linked glucose. It is a bacterial exopolysaccharide that is prepared commercially in a manner similar to xanthan gum.

In a preferred embodiment, the composition comprises cellulose. Preferably the present composition contains between 0.05 and 3 wt. % cellulose, based on total weight of the composition, preferably 0.1-2 wt. %, more preferably 0.3-1 wt. %. Cellulose is a linear homopolymer of anhydroglucose units linked together by beta-D-1,4 glycosidic bonds. It is preferred to select cellulose from the group consisting of high viscous cellulose and cellulose derivatives like hydroxyethyl cellulose, hydroxypropyl methylcellulose (HPMC), carboxymethyl cellulose (CMC), microcrystalline cellulose (MCC) and methyl cellulose. It was found that excellent results in terms of stability were obtained using large amounts of the non-ionic cellulose ether microcrystalline cellulose.

In this context it is important to differentiate between slowing precipitation of already formed particles and/or viscosity increase on the one hand, from a decrease in rate and/or prevention of the formation of particles on the other hand. In the present case, it is less important to stabilize already suspended particles. After all, in such case the formation of precipitates would still occur, since with time particles having a higher mass will reach the bottom of the package. In order to solve the problem of the invention, in a main aspect the thickener prevents and/or reduces the formation of the particles, and thus decreases the formation of a sediment on the bottom of a package.

Due to the limited water-solubility and/or dispersability of the non-ionic cellulose ether, it is preferred that the composition of the invention further contains a respectable amount of an anionic polymeric polysaccharide. In a preferred embodiment the anionic polysaccharide is selected from the group consisting of guar gum, carboxymethylcellulose, hemicellulose, pectin, alginate, konjac flour, psyllium, gums from tragacanth, xanthan, karaya, chia, wellan, ghatti or okra, or the hydrolysates of these oligo- or polycarbohydrates, These anionic polysaccharides facilitate the manufacture of a stable aqueous food product, in particularly a heat treated or sterilized liquid product which comprises nucleotides and one or more protein s. The anionic polymeric polysaccharide, such as guar gum or an anionic cellulose, enhances the stability of the aqueous system and prevents agglomeration of cellulose. In one embodiment, it is preferred to use an anionic cellulose, preferably carboxymethyl cellulose (CMC).

In a preferred embodiment, the liquid composition contains a mixture of MCC and an anionic polymeric polysaccharide, preferably CMC. The liquid composition preferably comprises 0.05-3.0 wt. % of a mixture of microcrystalline cellulose (MCC) and an anionic polymeric polysaccharide, based on the total weight of the composition, preferably 0.3-1.0 wt. %. The relative weight ratio of non-ionic cellulose to the anionic polymeric polysaccharide is preferably at least 3:1, more preferably between 4:1 and 9:1. In one embodiment, it is preferred that at least 70 wt. %, more preferably 75-90 wt. % of the cellulose thickeners present in the composition is provided by MCC. Often, MCC is marketed being coated with CMC or cellulose gum. In the most preferred embodiment, the remainder is formed from CMC. Suitable candidates are Avicel-plus-BV2312 and Vivapur MCG591F, commercially available with FMC biopolymers and Rettenmaier, respectively. Particularly good results are reported for the latter of the two.

It is further found that optimal characteristics were obtained with thickeners having a certain particle size. Preferably the present thickener is a mixture of particles wherein at least 50 wt. % of the particles have a particle size between 20 and 200 micrometer. The bigger thickener particle sizes avoid sedimentation to occur over longer time scales.

The inventors have discovered that the amount of the one or more cellulose thickeners in the liquid composition is preferably more than 0.05 wt. %, more preferably at least 0.1 wt. %, more preferably at least 0.3 wt. %, based on the total weight of the composition. It is believed that at these concentrations a weak three-dimensional network is built which effectively holds the components in the liquid matrix, the result being no sediment can form. In order to control the viscosity of the composition, it is preferred that the composition contains less than 1.0 wt. %, more preferably less than 0.8 wt. % of the cellulose thickener(s).

Apart from the cellulose, gellan and/or xanthan thickeners, it is preferred that the liquid nutritional composition is low in other thickening agents, i.e. substances that are known to increase the viscosity of a composition without substantially modifying its other properties, such as taste. It is preferred that the composition comprises less than 0.1 wt %, more preferably less than 0.05 wt. % of such other food thickeners, most preferably none at all. In one embodiment, the weight ratio of thickeners other than cellulose and xanthan over the sum of cellulose and xanthan thickeners of the present invention is less than 0.1, preferably less than 0.01, more preferably 0. More preferably, the weight of thickeners other than cellulose over the sum of the weight cellulose thickeners present in the composition is less than 0.1, more preferably less than 0.01, most preferably 0.

Physical Characteristics

The composition is preferably characterized by its rheologic behaviour. Thereto, viscosity measurements are performed using 'cup and bob' geometry or plate and cone geometry. A sample can be suitably analysed by using a MCR 300 rheometer (Anton Paar Physica, Graz, Austria).

Cup and bob viscometers work by defining the exact volume of sample which is to be sheared within a test cell, the torque required to achieve a certain rotational speed is measured and plotted. There are two classical geometries in cup and bob viscometers, known as either the "Couette" or "Searle" systems—distinguished by whether the cup or bob rotates. Either one may be used, to determine storage modulus G', loss modulus G" and loss factor with strain between 1-100% at 0.1 Hz at 20° C. The loss factor tan δ=G"/G'. By measuring G' and G" the structure strength is thus evaluated. The storage modulus and the loss modulus can be suitably determined using a DG 26.7 cup and massive cylinder (Anton Paar Physica, Graz, Austria). These amplitude sweep measurements can be carried out with a strain of 0.01-1000% and shear rate of 10 s$^{-1}$. Samples are preferably added to the cup at least 10 minutes before measurements are started.

It is found that good results are obtained with G' being larger than but close to G", i.e. 0.1<tan δ<100. In such case, sedimentation will be slowed down greatly or even avoided. With larger values, consumers would appreciate an unwanted "gel-like" taste, which may be described as a little bit sticky, slippery or slimy. Best results are obtained with tan δ<10, and more preferably tan δ is larger than 0.2. The value for tan δ should be within the aforementioned range at any strain between 1 and 100%, as measured at 0.1 Hz frequency and at 20° C. Within the range of 1-100% strain, an substantially linear relationship is observed. For sake of comparison, without the present thickeners G">G', which indicates a low viscosity product with little structural strength. It has a pure liquid character and tan δ>1000.

Even more preferably, tan δ also remains within the range of 0.1-100, preferably larger than 0.2, when measured similarly, but at strain 100-1000%.

The composition for use according to the invention preferably has a low viscosity, preferably a viscosity between 1 and 100 mPa·s measured at a shear rate of 100 sec$^{-1}$ at 20° C. High viscosities are to be avoided, since these often are associated with unacceptable mouthfeel characteristics and difficulty to be ingested by the target group, e.g. elderly and Alzheimers patients. More preferably, the present composition is preferably provided in the form of a drink capable of being ingested through a straw which makes the product even easier to ingest and improves compliance. In a preferred embodiment the present composition has a viscosity of less than 80 mPas at a shear rate of 100 per sec at 20° C., more preferably of 1-40 mPas at a shear rate of 100 per sec at 20° C. These viscosity measurements may be performed using plate and cone geometry. 'Cone and Plate' viscometers use a cone of very shallow angle in bare contact with a flat plate. With this system the shear rate beneath the plate is constant to a modest degree of precision and deconvolution of a flow curve; a graph of shear stress (torque) against shear rate (angular velocity) yields the viscosity in a straightforward manner.

It is preferred that the present composition fulfils FSMP guidelines, and hence contains significant amounts of minerals and vitamins. Hence, typically the product has an osmolality of 300 to 800 mOsm/kg.

To prevent increased viscosity due to gelling of protein the pH of the liquid is preferably kept around neutral, while for a good palatability the pH is preferably slightly acidic. The liquid nutritional composition preferably has a pH in the range of 5-7.5, more preferably 6-7.

The liquid nutritional composition preferably has a dry matter content in the range of 10-40 wt. %, more preferably 10-30 wt. %.

Nucleotides/Nucleosides

Preferably the present composition comprises nucleosides and/or nucleotides, preferably nucleotides. Nucleotides add to the phosphorus content and therefore cause similar problems if the product in which these are included in high amounts also contain protein and calcium. Nucleotides typically more effectively absorbed by the body. The liquid composition preferably comprises 80-3000 mg nucleotide and/or nucleoside per 100 ml liquid product, preferably 100-2000 mg nucleotide and/or nucleoside per 100 ml liquid product, more preferably 200-1000 mg nucleotide and/or nucleoside per 100 ml liquid product.

Preferably, the liquid composition is characterized by comprising predominantly nucleotides over nucleosides. So the mass ratio of nucleotides over nucleosides is preferably more than 2.0, more preferably more than 4.0, most preferably more than 10.0, in particular more than 20. These ratios are specifically preferred for liquid products with pH between 2.0 and 8.0, more preferably between 5-7.5, more preferably 5.5-7.5, most preferably 6-7.

The present inventors have found that the invention works particularly well when the composition comprises uridine nucleotide or uridine nucleoside, preferably uridine nucleotide, preferably at least one uridine phosphate selected from uridine monophosphate (UMP), uridine diphosphate (UDP) and uridine triphosphate (UTP).

Also, the present composition preferably comprises cytidine nucleotide or cytidine nucleoside, preferably cytidine nucleotide, preferably at least one cytidine phosphate selected from cytidine monophosphate (CMP), cytidine diphosphate (CDP) and cytidine triphosphate (CTP).

Most preferably the present composition comprises UMP, as UMP is most efficiently being taken up by the body. Additionally, it was surprisingly found by the inventors that UMP contributes to the product stability, since it binds calcium and thus reduces calcium-induced protein aggregation even further.

Hence, inclusion of UMP in the present product enables a high efficacy at the lowest dosage and/or the administration of a low volume to the subject. Preferably at least 50 wt. % of the uridine in the present composition is provided by UMP, more preferably at least 75 wt. %, most preferably at least 95 wt. %. The liquid composition preferably comprises 0.08-3 g uridine per 100 ml, preferably 0.1-2 g uridine per 100 ml day, more preferably 0.2-1 g uridine per 100 ml, wherein uridine is the cumulative amount of uridine, deoxyuridine, uridine phosphates, uracil and acylated uridine derivatives.

The present liquid composition preferably comprises 0.08-3 g UMP per 100 ml liquid product, preferably 0.1-2 g UMP per 100 ml liquid product, more preferably 0.2-1 g per 100 ml liquid product. Preferably 1-37.5 mg UMP per kilogram body weight is administered per day.

Preferably the weight ratio of uridine to cytidine is larger than 1.0, more preferably at least 2.0, most preferably more than 5.0. The term cytidine as used herein relates to cytidine and/or equivalent thereof. Although cytidine is a precursor of uridine, which passes the blood brain barrier, it is more efficient and effective to include uridine in the present composition.

In a further preferred embodiment the present composition preferably does not contain high amounts of other nucleotides. Hence, preferably the weight ratio adenosine/uridine in the present composition is below 0.1, more preferably below 0.01, most preferably 0. Preferably the weight ratio guanosine/uridine in the present composition is below 0.1, more preferably below 0.01, most preferably 0. Preferably the weight ratio of inosine to uridine in the present composition is below 0.1, more preferably below 0.01, most preferably 0.

Choline

The combination of uridine with choline is particularly effective in improving neurodegenerative disorders, particularly in improving membrane formation and memory function. Hence preferably the present composition contains a component selected from the group consisting of choline (including choline salts, e.g. choline chloride), citicholine, cytidylcholine and phosphatidylcholine, more preferably choline and/or phosphatidylcholine, more preferably choline. Supplying choline with the diet increases the plasma choline and thereby prevents or slows down membrane breakdown, and increases new membrane synthesis. The use of the selected methyl donors will increase the number of patients that respond to the therapy. Especially elderly, in particular frail elderly, benefit from the inclusion of the selected choline.

The inclusion of choline however provides additional challenges with respect to sedimentation, as the further inclusion of salts such as choline chloride further increases the risk of sediment formation. It was found that also when choline (salt) was included in the present composition with thickener, no sediment was formed.

The present composition preferably comprises 50 mg to 3 gram choline per 100 ml of the liquid formula, preferably 200 mg-1000 mg choline per 100 ml. The choline composition is preferably comprises choline chloride.

Minerals

To fulfil important nutritional requirements the present liquid composition contains divalent cations, particularly calcium. Preferably the present liquid composition contains 10-150 mg calcium per 100 kcal, preferably 40-100 mg calcium per 100 kcal. Alternatively or additionally, it is preferred for the liquid composition to contain 10-150 mg calcium per 100 ml, more preferably 40-100 mg calcium per 100 ml. The calcium causes particular problem in aggregation of proteins. Hence, the present composition preferably comprises an insoluble calcium source. In a preferred embodiment, the calcium salt (s) used in the present composition have a solubility below 0.15, more preferably below 0.1, even more preferably below 0.06 gram per 100 ml (demineralised) water at 20° C. and pH 7.

The calcium salt is preferably selected from the group consisting of calcium carbonate, calcium sulfate, calcium citrate (e.g. mono-calcium citrate or tri-calcium citrate), a calcium salt coated with a substance which has limited solubility in water at pH 7 and is soluble at a pH below about 5 (hereafter referred to as coated calcium salts) and mixtures thereof. Examples of coatings and methods for the preparations of coated calcium salts are given in W00/038829, the entire content of which is hereby incorporated by reference. Preferably the present composition comprises calcium citrate.

In certain embodiments, particularly for compositions containing low amounts of nucleotides or nucleosides, it is be desirable to add phosphate salts. The phosphate salt can be added to provide the mineral requirements to a patient. Preferably the present composition contains phosphate salts of sodium, potassium, calcium and/or magnesium. The composition preferably comprises 30 to 80 mg phosphorus per 100 kcal.

LC-PUFA

The present composition preferably contains docosahexaenoic acid (22:6 ω-3; DHA), and/or eicosapentaenoic acid (20:5 ω-3; EPA). The present liquid composition preferably contains 100-5000 mg (DHA+EPA) per 100 ml, more preferably 500-3000 mg per 100 ml. The present composition preferably contains a very low amount of arachidonic acid (AA; 20:4 ω-6). The arachidonic acid is believed to counteract the effects of the present composition. The present subjects normally ingest sufficient and/or biosynthesizes (precursors of) AA, and an excess daily dosage may stimulate inflammatory responses, inhibiting daily activities. Preferably the weight ratio DHA/AA in the present composition is at least 5, preferably at least 10, more preferably at least 15. The present method preferably comprises the administration of a composition comprising less than 5 wt. % arachidonic acid based on total fatty acids, more preferably below 2.5 wt. %. The ratio omega-6/omega-3 fatty acids in the present product, is preferably below 0.5, more preferably below 0.2.

Protein

The present composition comprises protein, preferably intact protein. Proteins enable the manufacturing of palatable products. Especially for elderly and AD patients benefit from the protein as it strengthens the motor skills. Preferably the present composition comprises milk protein. Preferably the present composition comprises a protein selected from the group consisting of whey protein, casein or caseinate. Preferably the present composition comprises caseinate, more preferably the present composition contains at least 70 wt. %, more preferably at least 90 wt. % casein and/or caseinate based on total protein.

Preferably, the proteins are included in intact (unhydrolyzed) form, in order to have a palatable product. Such high molecular weight proteins increase the viscosity of the heat-treated liquid product, compared to the hydrolyzed forms. The present inventors were able to make an acceptable product, with good palatability and limited viscosity, by applying the measures according the invention, still avoiding precipitation.

Preferably the present composition contains between 0.2 and 7 gram protein per 100 ml, preferably, more preferably between 1 and 6 grams protein per 100 ml, most preferably between 2 and 5 grams protein per 100 ml.

Other Components

Preferably, the present composition preferably comprises phospholipids, preferably 0.1-50 wt. % phospholipids based on total weight of lipids, more preferably 0.5-20 wt. %, more preferably between 1 and 5 wt. % based on total weight of lipids. Preferably the present composition contains at least one selected from the group consisting of phosphatidylcholine, phosphatidylethanolamine, phosphatidylserine and phosphatidylinositol. The total amount of lipids is preferably between 10 and 30 wt. % on dry matter, and/or between 2 and 6 g lipid per 100 ml for a liquid composition. Inclusion of phospholipids beneficially improves membrane function, thereby enabling an improved functioning of the different parts of the brain that play a (main) role in the ability to perform daily activities. Furthermore, the phospholipids improve stability of the present product.

Advantageously the present composition contains digestible carbohydrates. The digestible carbohydrates positively influence the operational skills of the subject, and have an advantageous effect over and above the effects for the present composition containing uridine. The present composition preferably contains between 1 and 50 gram digestible carbohydrates per 100 ml of a liquid product, more preferably between 5 and 30 grams per 100 ml, more preferably 10-30 grams carbohydrates/100 ml. The total amount of digestible carbohydrates is preferably between 25 and 80 wt. % on dry matter, preferably 40-80 wt. %.

Preferably the present composition contains organic acid(s), preferably 0.5 to 10 wt. % organic acid based on total weight of digestible carbohydrates, more preferably 1.5 to 6 wt. %. Preferably the present composition contains citric acid, preferably 0.5 to 10 wt. % citric acid based on total weight of digestible carbohydrates, more preferably 1.5 to 6 wt. %.

Persons suffering from neuropathies or neurological problems often experience problems with eating. Their sensory capabilities and/or control of muscles have become imparted, as well as, in some instances, their ambition to apply proper eating habits. Part of these patients may experience a general loss in appetite and a relatively large part of this patient group became malnourished. Preferably the product has an energy density of 0.8-4.5 kcal per g of the composition, more preferably between 0.9 and 2.5 kcal per ml.

Liquid nutritional products preferably have a long shelf life. However, increasing shelf life by heat treatments often results in destabilisation of the products and/or palatability, leading to a product which is unacceptable. The present liquid product can be subjected to a heat treatment without major adverse side effects. Hence, the present liquid composition is preferably heat-treated, more preferably the composition is subjected to a sterilization process. In a preferred embodiment the present composition is subjected to an ultra-high temperature treatment (UHT-process). Such UHT-process is preferably applied in line, i.e. before the liquid product is filled in the package of the sold unit.

Application

The invention particularly pertains to the use of the above-defined liquid composition for preventing and/or treating neurodegenerative disorders, preferably selected from the group consisting of memory decline and/or cognitive dysfunction, Alzheimer's, Parkinson's and/or dementia. In the context of the invention, "dementia" is especially understood "senile dementia". Senile dementia or dementia is considered to comprise Alzheimer's disease (AD). The invention also pertains to the use of the aforementioned composition for promoting or supporting healthy brain function.

The composition is particularly useful for the dietary management of subjects suffering from neurodegenerative disorders, preferably selected from the group consisting of memory decline and/or cognitive dysfunction, Alzheimer's, Parkinson's and/or dementia.

The present method preferably comprises the administration of between 25 and 500 ml of the present composition, preferably between 50 and 250 ml, preferably between 75 and 150 ml. Preferably this is administered once a day. Relatively limited volumes are easy to ingest by the target patients groups, e.g. elderly and AD patients.

The invention also pertains to the treatment and/or prevention memory impairment, particularly the treatment and/or prevention of age-associated memory impairment (AAMI), Mild Cognitive Impairment (MCI), significant episodic memory impairments, prodromal dementia and/or prodromal Alzheimer, and/or to treating elderly with memory and/or cognitive impairments, using the aforedefined composition.

It is also an objective of the invention to provide a method for preventing and/or treating one of the aforementioned disorders or for supporting brain health in a subject in need thereof, by administering to said subject the liquid composition as defined above. The patient is preferably a person older than 50 years of age.

EXAMPLE 1

Sedimentation of the UMP-Containing Product without Thickener

A liquid formula containing per 100 ml: Energy 100 kcal Protein 3.06 g (casein, whey 80/20) Carbohydrates 13.3 g (maltodextrins, sucrose) Fat 3.73 g (fish oil, phospholipids) comprising 0.96 g DHA and 0.24 g EPA; Uridine monophosphate 0.5 g (disodium salt); Choline 0.32 g; Vitamin E 32 mg alpha-tocopherol Vitamin C 64 mg Selenium 48 mcg; Vitamin B6 0.8 mg; Folic acid 0.32 mg; Vitamin B12 2.4 mcg; Magnesium 20 mg; Zinc 1.2 mg; Manganese 0.3 mg; Molybdenum 10 mcg; 0.1 g Na; 0.15 g K; 0.12 g Cl; 80 mg Ca; 70 mg P; 1.6 mg Fe; 27 mcg I; 0.18 mg Cu; 6.7 mcg Cr; 0.1 mg F; 0.16 mg vit A; 0.15 mg B1; 0.16 mg B2; 1.8 mg B3; 0.53 mg B5; 0.7 mcg D; 4.0 mcg biotin; and 5.3 mcg vitamin K; was tested for sediment formation. Surprisingly the product was tested negative for sediment formation after incubation at 0 months, minor sediment formation after 1 month, significant sediment formation after two months and high amounts of large sediment particles after 4 months (see Table 1)

TABLE 1

| Time (Months) | Incubation temperature (° C.) | Sediment formation (Visual after sieving with 150 micron sieve) |
|---|---|---|
| 0 | 20 | -- |
| 1 | 37 | +/- |
| 2 | 20 | + |
| 4 | 37 | ++ |
| 5 | 37 | ++ |

EXAMPLE 2

Sedimentation of the UMP-Containing Product with Different Concentrations of Thickener The product described in example 1 was tested for sediment formation using different concentrations of thickener (Avicel-plus-BV2312 (mix of 85-92 wt. % cellulose gum and 8-15 wt. % CMC). It was found that already relatively small amounts of the thickener prevented sedimentation (see Table 2). Sedimentation was evaluated using 150 micron sieve.

TABLE 2

| Time (Months) | Incubation temperature (° C.) | Concentration thickener (w/w) | | | | | |
|---|---|---|---|---|---|---|---|
| | | 0.0% | 0.10% | 0.2% | 0.3% | 0.4% | 0.5% |
| 0 | 20 | -- | -- | -- | -- | -- | -- |
| 1 | 37 | ++ | + | -- | -- | -- | -- |
| 2 | 37 | ++ | + | -- | -- | -- | -- |
| 4 | 20 | ++ | -- | -- | -- | -- | -- |

EXAMPLE 3

A Liquid Formula with the Composition According to Example 1, and 0.4 g Vivapur MCG591F (Mix of 85-91 wt. % Cellulose Gum and 9-15 wt. % CMC) per 100 ml Water The rheology properties of the thickener-containing formula in terms of the loss factor tan δ was about 1, even after several months. G' and G" were between 10 and $10^3$. The corresponding counterpart free from thickeners exhibited values of $10^{-3}$, 1 and $10^4$ for the storage modulus, loss modulus and loss factor, respectively.

These numbers were roughly obtained over the whole range of 1-100% strain at 0.1 Hz and 20° C., using a 'cup and bob' (cylinder geometry) Physica Couette-type viscometer (Physica US200, USA).

The thickener-containing product was tested for the formation of sediments over time. No sediment formation occurred for an incubation period of 8 months (at 20° C. and 37° C.). This is indicative for the advantageous solution the present invention provides.

The invention claimed is:

1. A method for treating memory decline and/or cognitive dysfunction, Alzheimer's disease, Parkinson's disease and/or dementia, the method comprising administering to a person in need thereof a composition comprising:
   (i) at least 50 mg nucleoside and/or nucleotide per 100 ml of the composition;
   (ii) between 0.2 and 10 grams protein per 100 ml of the composition; and
   (iii) between 0.05 and 3 wt. % of thickener, based on total weight of the composition, wherein the thickener is selected from the group consisting of cellulose, xanthan gum and gellan gum, and mixtures thereof.

2. The method according to claim 1, wherein the thickener comprises cellulose.

3. The method according to claim 1, wherein the composition comprises a mixture of microcrystalline cellulose (MCC) and an anionic polymeric polysaccharide.

4. The method according to claim 3, wherein the mixture comprises 0.05-1.0 wt % of the composition.

5. The method according to claim 3, wherein the anionic polymeric polysaccharide is carboxymethyl cellulose (CMC).

6. The method according to claim 1, wherein the composition has a loss factor tan δ between 0.1 and 100, as measured at any strain in the range of 1-100% at 0.1 Hz and 20° C.

7. The method according to claim 1, wherein the composition has shear-thinning and/or thixotropic properties.

8. The method according to claim 1, the composition further comprises between 10 and 150 mg calcium per 100 kcal.

9. The method according to claim 1, wherein the composition comprises nucleotide, wherein the nucleotide and provides at least 30 wt. % of total phosphorus in the composition.

10. The method according to claim 8, wherein (a) nucleotide provides at least 30 wt. % of total phosphorus in the composition or (b) the composition comprises a weight ratio of protein to calcium of at least 5.

11. The method according to claim 8, wherein the composition comprises a weight ratio of protein to calcium of at least 10.

12. The method according to claim 1, wherein the composition comprises a dry matter content between 10 and 40%.

13. The method according to claim 1, wherein the composition comprises at least one cellulose selected from the group consisting of hydroxyethyl cellulose, hydroxypropyl methyl cellulose, carboxymethyl cellulose, microcrystalline cellulose and methyl cellulose.

14. The method according to claim 1, wherein the composition comprises uridine monophosphate (UMP) in an amount of 0.08-3 g per 100 ml of the composition.

15. The method according to claim 1, wherein the composition further comprises 50 mg to 3 gram choline per 100 ml of the composition.

16. The method according to claim 15, wherein the choline is in the form of choline chloride.

17. A liquid composition comprising:
   (i) at least 50 mg nucleoside and/or nucleotide per 100 ml of the composition;
   (ii) between 0.2 and 10 grams protein per 100 ml of the composition; and
   (iii) between 0.05 and 3 wt. % of thickener, based on total weight of the composition, wherein the thickener is selected from the group consisting of cellulose, xanthan gum and gellan gum, and mixtures thereof.

18. The liquid composition according to claim 17, wherein the composition has a loss factor tan δ between 0.1 and 100, as measured at any strain in the range of 1-100% at 0.1 Hz and 20° C.

19. The liquid composition according to claim 17, further between 10 and 150 mg calcium per 100 kcal.

20. The liquid composition according to claim 17, comprising nucleotide, wherein the nucleotide provides at least 30 wt. % of total phosphorus in the composition.

21. The composition according to claim 19, wherein (a) nucleotide provides at least 30 wt. % of total phosphorus in the composition or (b) the composition comprises a weight ratio of protein to calcium of at least 5.

22. The composition according to claim 19, wherein the composition comprises a weight ratio of protein to calcium of at least 10.

23. The composition according to claim 17, wherein the thickener comprises cellulose.

24. The composition according to claim 17, wherein the composition comprises a mixture of microcrystalline cellulose (MCC) and an anionic polymeric polysaccharide.

25. The composition according to claim 24, wherein the mixture comprises 0.05-1.0 wt % of the composition.

26. The composition according to claim 24, wherein the anionic polymeric polysaccharide is carboxymethyl cellulose (CMC).

27. The composition according to claim 17, wherein the composition has shear-thinning and/or thixotropic properties.

28. The composition according to claim 17, wherein the composition comprises a dry matter content between 10 and 40%.

29. The composition according to claim 17, wherein the composition comprises at least one cellulose selected from the group consisting of high viscous cellulose and cellulose derivatives.

30. The composition according to claim 17, wherein the composition comprises hydroxyethyl cellulose, hydroxypropyl methyl cellulose, carboxymethyl cellulose, microcrystalline cellulose and methyl cellulose.

31. The composition according to claim 17, wherein the composition further comprises uridine monophosphate (UMP) in an amount of 0.08-3 g per 100 ml of the composition.

32. The composition according to claim 17, wherein the composition comprises 50 mg to 3 gram choline per 100 ml of the composition.

33. The composition according to claim 32, wherein the choline is in the form of chloline chloride.

* * * * *